(12) United States Patent
Westermann et al.

(10) Patent No.: US 8,965,777 B2
(45) Date of Patent: Feb. 24, 2015

(54) COMMUNICATIONS SYSTEM FOR ARTICLES OF CARE FURNITURE

(75) Inventors: Karsten Westermann, Sønderborg (DK); Peter Brøndum Jensen, Sønderborg (DK)

(73) Assignee: Linak A/S, Nordborg (DK)

( * ) Notice: Subject to any disclaimer, the term of this patent is extended or adjusted under 35 U.S.C. 154(b) by 226 days.

(21) Appl. No.: 12/998,430

(22) PCT Filed: Oct. 27, 2009

(86) PCT No.: PCT/DK2009/000225
§ 371 (c)(1),
(2), (4) Date: Apr. 20, 2011

(87) PCT Pub. No.: WO2010/048953
PCT Pub. Date: May 6, 2010

(65) Prior Publication Data
US 2011/0202364 A1    Aug. 18, 2011

(30) Foreign Application Priority Data

Oct. 27, 2008  (DK) .................................. 2008 01479
Nov. 17, 2008  (DK) .................................. 2008 01605

(51) Int. Cl.
*G06Q 50/22* (2012.01)
*G06F 19/00* (2011.01)

(52) U.S. Cl.
CPC ............. *G06F 19/327* (2013.01); *G06Q 50/22* (2013.01)
USPC ............................................................ 705/2

(58) Field of Classification Search
CPC ........................................................ G06Q 50/22
USPC ............................................................. 705/2
See application file for complete search history.

(56) References Cited

U.S. PATENT DOCUMENTS

| | | | |
|---|---|---|---|
| 7,348,883 B2 * | 3/2008 | Sloan | 340/568.1 |
| 7,664,657 B1 * | 2/2010 | Letzt et al. | 705/2 |
| 2002/0044043 A1 * | 4/2002 | Chaco et al. | 340/286.07 |
| 2003/0163535 A1 | 8/2003 | Suzuki | |
| 2006/0049936 A1 * | 3/2006 | Collins et al. | 340/539.11 |
| 2007/0057014 A1 | 3/2007 | Whitman et al. | |
| 2008/0018436 A1 * | 1/2008 | Traughber et al. | 340/286.07 |

* cited by examiner

*Primary Examiner* — Michael Fuelling
(74) *Attorney, Agent, or Firm* — Dykema Gossett PLLC

(57) ABSTRACT

Communications system for exchanging data between a patient in an article of care furniture and a nursing staff or service personnel which manages a nursing task for the patient or a service function of the article of care furniture, where the control communicationwise is connected to a gateway, which comprises a modem for communication between a patient and the nursing staff or service personnel via the mobile telephone network where the communication is carried out by exchanging data in the form of text strings. The patient may with his actions or by activating a switch initiate the transmittal of a text string. When receiving a text string on a mobile receiver, the nursing staff may, based on the contents of the text string, determine whether the visiting route should be changed so that a more acute nursing task may be given a higher priority.

11 Claims, 2 Drawing Sheets

COMMUNICATIONS SYSTEM FOR ARTICLES OF CARE FURNITURE

BACKGROUND OF THE INVENTION

1. Field of the Invetion

The present invention relates to a care bed for communication between a patient and nursing staff or service personnel.

2. The Prior Art

The invention mainly relates to communication between a patient who, due to illness is dependent on regular care, and the nursing staff which manages this task. When their mobility is reduced, such patients may have to stay in a hospital or care bed or another article of furniture, e.g., a chair or a wheel chair, for a long period of time. The term communication is used to not only refer to direct oral communication between a patient and a nursing attendant, but also to include the exchange of data describing a patient's needs and data describing the state of both the patient and the article of care furniture.

Hospital systems for communication between a patient and the nursing staff are known. In the most simple embodiment, it is a switch which can be activated by the patient as an emergency call or when assistance is required. More sophisticated systems are known where a number of parameters concerning the state of the patient and the hospital bed are continuously transferred to a central monitoring. In most cases it is a wired connection with a plug connection between the bed and a wired network connection from the central monitoring to the room in which the patient is located. However, systems are known like, e.g., US 2008/205311 A1 to Perkins et al., where the interface between the bed and the network over a short range has been replaced by a wireless connection.

As another example of a communications system, a hospital system as known from US 2003/0163535 A1 may be mentioned, which relates to a communications system where the patient by operating a switch can send preselected e-mail messages to relatives in that this function is supported by the central monitoring system.

In a hospital with limited geographical dispersal, such a monitoring system is practical as it is relatively simple to connect the beds to a central network via cables or short-range wireless networks.

For patients living in sheltered accommodations or in their own homes, such a system is difficult to use, as it would result in a large amount of wiring and installation and typically require a connection to the central monitoring with a modem via a telephone connection. The problem is further complicated by the fact that the patient over periods can change between being placed in a care bed, a chair or a wheel chair, which cannot readily be connected to a wired network. Therefore, the communication between a patient and the nursing staff is often limited to regular phone calls, where the patient is in contact with the nursing staff or a central switch board. Further, it is to be expected that the nursing staff travels over a large geographical area between the patients, for which reason wired telephone connections for contact with the patients are difficult to use. Another factor is that the nursing staff as far as possible should be spared telephone calls, so that they can focus on the ongoing nursing task instead. Normally a scheduled route is followed between the patients to minimize the commuting time and thus both the expenses for hourly wages and the expenses for running the utilized vehicles. Some conditions would, however, require that the nursing staff will have to prioritize the patient and change the scheduled route, e.g., if a non-mobile patient leaves the article of care furniture or if an accident has occurred, where the patient has contaminated the article of care furniture with body fluids. On ethical and health grounds, mainly to avoid bedsores, it would be required that the nursing staff as soon as possible pays the patient a visit.

The purpose of the invention is to provide an alternative solution to the personal telephone contact between a patient in a sheltered accommodation or his own home and the nursing staff when the patient requires attendance, where the patient in an easy and secure manner can call the mobile nursing staff for assistance without interrupting them for long periods of time during their ongoing nursing tasks but still makes it possible to change the visiting route and thus prioritize the patient.

SUMMARY OF THE INVENTION

This is achieved according to the invention by designing the communications system for exchanging data between a patient in an article of care furniture and the nursing staff managing a nursing task for the patient in such a way that the article of care furniture communicationwise by means of the control is connected to a gateway which comprises a modem for communication between the patient and the nursing staff or service personnel via the mobile telephone network, where the communication is carried out by exchanging data in the form of text strings.

In that the gateway is connected to the control via an interface, it is thus possible to transfer status, alarms and activations of the operation panel from the control to the gateway, which subsequently transmits the piece of information as a data string, preferably a text string, via the mobile telephone network. An appropriate interface for the control when connecting to the gateway and other equipment could be OPENBUS™ as described in WO 2007/057014 A1 to Linak A/S.

An article of care furniture could be a hospital or care bed, a chair or a wheel chair, but is here described as being a bed. Hospital or care beds are characteristic in that it is possible to adjust different parameters of the bed in order to provide more comfort for both the patient and the nursing staff when they perform a nursing task. It could be the height or lying surface of the bed. For effecting the adjustment, the article of furniture is equipped with the control. However, the communication system may also be used in connection with a non-adjustable bed or another article of furniture, e.g., an armchair. It is thus preferred that the gateway is equipped with input to receive signals from the affiliated equipment. For the control and the gateway, the affiliated equipment can be an operation panel or sensors, e.g., a sensor which detects whether the patient currently occupies the article of furniture, a sensor which detects whether the bed needs cleaning, or a sensor which detects if the patient has wet the bed.

Expediently, the data string is provided in the format which is compatible with the message service in the mobile telephone network in question. It could, e.g., in the GSM (Global System for Mobile communications) system be a text string sent as a SMS (Short Message Service), where each SMS contains a text string of one hundred and sixty characters.

When required more SMS messages may be compiled to an EMS (Enhanced Messaging Service) and thus generate a longer text string.

Where the data communication between the article of care furniture for the patient and the nursing staff is more extensive, a package-based transmittal of data may advantageously be used, as this form of communication is often more inexpensive than message services, as it is the traffic volume and not the number of messages which is paid for. In the GSM system it could be GPRS or E-GPRS, which describes standards for transmittal of data packages between two terminals via the network.

The text strings are sent to at least one receiver connected to the mobile telephone network. In order to be able to send the text strings to the correct receiver, the control or the gateway must be equipped with a list of numbers for the receiver or receivers to which the text string should be sent. Expediently, the list could be modified so that a general duty roster is automatically downloaded and used when the nursing staff changes shift. In that the gateway can also receive text strings from a remote unit, it is possible with a simple text message to be able to modify the duty roster, so that the phone number for the nursing staff is updated and matches the duty roster in the monitoring system. The information on the number for receiver/receivers of text strings are updated in the control by receiving a configuration text string with a special data structure which is recognized by the control.

A receiver for receiving a text string from the gateway may expediently be a conventional mobile telephone, which is featured by having a display where the text string can be viewed. This is particularly expedient as the nursing staff not necessarily will have to be in direct contact with the patient sending the text string. The nursing staff may swiftly read the message and then decide which action should be taken. It is a great advantage if the receiver sends an acknowledgement of receipt for the text string. This can be done either manually or automatically, and at different levels. The receiver in the form of a mobile telephone may e.g., be set to automatically confirm that the text string has been received; thereupon that it has been read. A message in the form of a text string can further be sent back to the patient containing information that the text string has been read and that the nursing staff is on the way. This will calm the patient, so that he will not continue sending text strings requiring attendance. In an embodiment the control will expediently be equipped with a filter, which prevents repeated sending of the same text string requiring attendance. The filter can either be a permanent filter or a filter which is activated when the nursing staff has sent a receipt for the received text string.

In connection with receiving text strings on the receiver for the nursing staff, it can be challenging to read this text string on a display, which especially is the case when the nursing staff is occupied by a nursing task or travelling in a car on their way to the next patient on the visiting route. The same applies when the patient receives a receipt for a sent request for attendance. Due to the state of the patient, who might be weakened due to age, it can be difficult to read a message on a display. It is thus advantageous that the receiver has means for converting the received text into speech either as soon as the text string is received or when activating this function by operating the mobile telephone. In mobile telephones or modems which are equipped with a java-engine for processing user applications, such a function may be designed as an extra portion of program code, in the form of a program with access to the resources of the mobile telephone, so that the text string may be retrieved from the memory of the mobile telephone and be converted into an audio file which may be played through the loudspeaker via the built-in multimedia function of the mobile telephone.

In another embodiment the communication uses MMS which is a further development of the message format SMS from the GSM system. MMS is characterized by being a message which does not only contain a text string but also information for reproduction of a graphic image and an audio file. The control or the gateway may thus contain a number of ready-made MMS messages which, depending on which function of the control is activated, may be sent to the receiver. It would be particularly expedient if the mobile telephone which is configured to receive the MMS messages also is set to automatically play the messages immediately upon receiving them so that the nursing staff or the patient, depending on which party receives the message, without operating the receiver in the form of a mobile telephone or modem, can hear and comprehend the message.

The receiver may also be a modem connected to a computer system which functions as a monitoring central. When the text string is received, it is converted into a file, which is received by the monitoring central. Depending on the configuration of the monitoring central the text string may expediently be stored in a log file, preferably in a database, so that it is relatively easy later to sort data and extract data with specific search criteria. An example of an extract of data could be the number of times the system has detected that a non-mobile patient has left the bed. Data can then be used to determine whether the patient in connection with personal care requires more attendance from the nursing staff so that this may be incorporated into the visiting route.

The monitoring system is moreover characterized in that it based on data in the received text string and data contained in a log file sorts and forwards the text string to a specific recipient, who handles the task specified in the text string. An example could be a mechanical problem in connection with the adjustable parts of the bed, which in order to be repaired requires a visit from a service technician. The text string can be forwarded directly as a message to a receiver in the form of a mobile telephone or to a computer system which handles and delegates service tasks.

To ensure that patients and articles of care furniture receive the necessary care and service, the system is designed so that a text string from a patient concerning the need for care is both send directly to the nursing staff according to the duty roster updated in the gateway and also to the monitoring system. It is therefore expedient that a receipt from the nursing staff confirming a received text string is not just sent to the receiver of the patient but also to the monitoring system, so that the system always has an updated list of outstanding tasks and which attendant has taken on the task. Thus, it is ensured that all requests for care are complied with, in that the system automatically after a while will send a reminder of an unanswered nursing task to the nursing staff or if necessary forward the request for care to another team which takes over the nursing task.

In that the nursing staff when they arrive at the address of the patient, from the patient's mobile equipment sends a text string to the monitoring system indicating that they have arrived at the location and are ready to begin the nursing task, the monitoring system is informed of the ongoing task of the nursing staff. As a text string is also sent from the patient's mobile equipment to the monitoring system after the task has been completed, the monitoring system always has an updated picture of which nursing tasks has been completed and how efficiently the nursing staff handles its task. Further it is achieved that the system can generate an expression for the load of the nursing staff attending to a specific visiting route, so that the administrative personnel is better prepared for establishing tasks and routes for a nursing team.

Another advantage of using a gateway with a GSM modem for an article of care furniture is the possibility to trace their geographical location. Hospital and care furniture are fairly expensive and are typically financed and lent out by the healthcare services. However, it happen that articles of care furniture, when they are no longer in use, are disposed of by relatives without the relatives necessarily being aware of the ownership. A GSM modem connects to the GSM system in that the modem continuously measures the signal strength for the closest accessible base stations and updates a list with information about these and the quality of the connection. When the modem is moved, a request for connection is sent to the base station which most clearly receives the signal from the modem. This list may also be used to determine the geographical location of the modem relative to the base stations. To be able to locate the modem and thus the bed, it would therefore be helpful if the gateway automatically when the control is connected to the mains supply sends one or more SMS messages containing this information to the monitoring system. It is possible to find the geographical location of the article of care furniture even though the signal strength fluctuates in relation to the percentage of building and this is with an accuracy of calculating the location of the modem of less than one hundred meters, typically ten meters. If the gateway is equipped with a GPS receiver more accurate coordinates can be sent in the same way via SMS.

The communications system may expediently be designed in such a way that it allows for oral communication (voice-calls) between the patient and the nursing staff. This is possible when the communications system is equipped with means for converting an audio signal into an electrical signal and further has means for converting an electrical signal into an audio signal. These means may e.g. be a microphone and a loudspeaker, or a unit which can change function between functioning as a microphone and a loudspeaker. Separate units are preferred. Such a microphone and loudspeaker can practically be built into the bed e.g. in an operation panel mounted on the bed. Further it is a condition that the GSM-modem is equipped with the necessary audio interfaces, i.e. an input with analog-digital converter and an output with digital-analog converter. There should also be a control, which controls the routing of the speech information in the established connection. In the simplest embodiment the patient can activate the function by pressing a call button, which will attempt to establish a connection between the built-in modem and the receiver of the nursing staff. This will be regarded as a voice-call, where the nursing staff as usual can see the caller-ID and choose to answer the call. However, is often unwelcome that the nursing staff receives calls, as it may disturb the staff in their ongoing task. It would thus be more expedient if the activation of a call button and the activation of other functions at the patient, e.g. an "out of bed detection", will initiate the sending of a text string specifying the incident. The nursing staff may thus choose to call the patient to establish a connection for oral communication. This it done simply by answering the incoming text message by activating a call to the sender of the text. In that the directory number for the terminal of the nursing staff when receiving a call is automatically compared to a list of acceptable numbers, and recognized by the patient's receiver as an acceptable incoming call, automatic pick up may be established, so that the connection between the terminal of the nursing staff and the terminal of the patient is established. This configuration prevents that unauthorized persons calls the patient and disturbs his privacy. Even though the communication described here is between a patient and the nursing staff, other authorized personnel can also call the patient. This could e.g. be a nurse, doctor or another contact person who needs to get in contact with the patient. An incoming call may as described above be received and established by automatic pick up. It is also possible to differentiate, so that automatic pick up is only established for certain chosen incoming calls based on their directory number, where other incoming calls are indicated by a ring tone and should be accepted as usual e.g. by activating a button. This could be a button dedicated to this purpose.

In a further embodiment the beds are equipped with a short range wireless data network (WPAN) such as Bluetooth at which a dynamic addressing becomes possible. When a person listed in the duty roster comes within reach of the wireless data network, that person's mobile telephone or mobile unit will automatically be registered so that if a signal is received from that area that person would be called instead of the person dedicated in the duty roster. Thus, the patient will receive quick assistance and the called person can quickly form an idea of which type of assistance is necessary. As the signals from the wireless network (WPAN) can go through walls and storey partitions, it is expedient to equip the beds with identification, e.g., IRID or RFID, to ensure that the signal is really sent from that area and not from the building next door or a floor above or below.

BRIEF DESCRIPTION OF THE DRAWINGS

An embodiment of the invention will be described more fully below with reference to the accompanying drawings, in which.

DETAILED DESCRIPTION OF THE PREFERRED EMBODIMENTS

Figure 1:
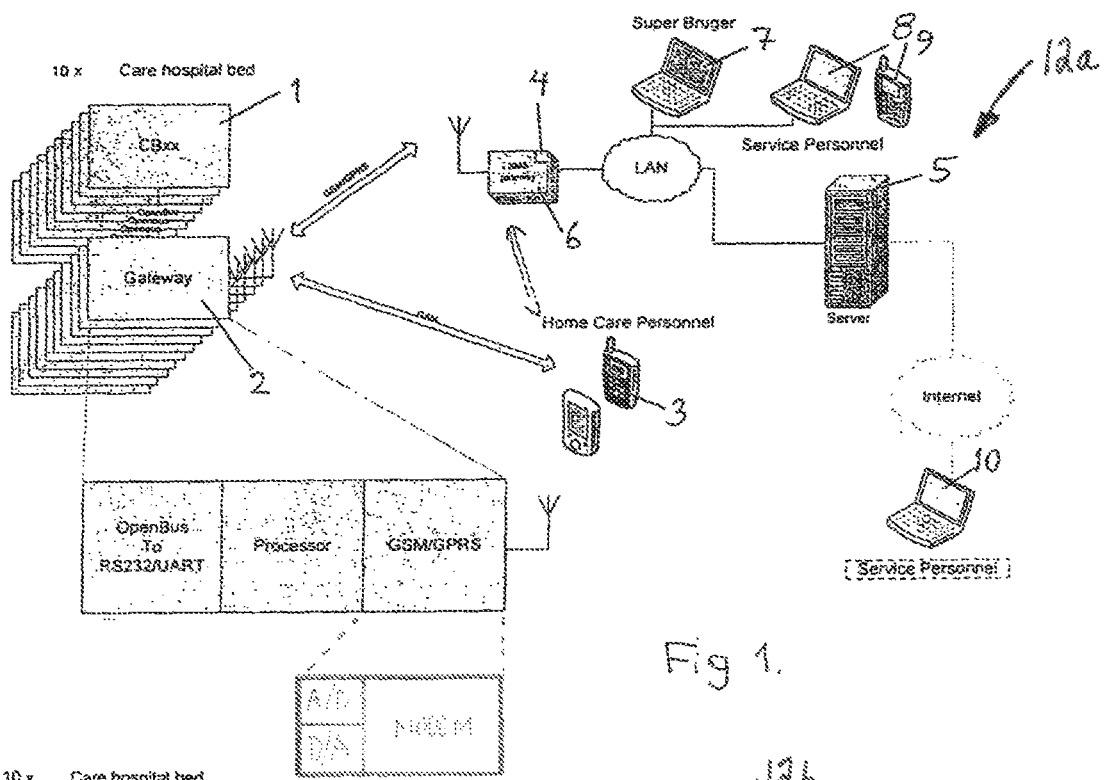
FIG. 1 shows a systems specification for the structure of the communications system.

FIG. 1 shows an overview of the communications system for communication between a patient in an article of care furniture and the nursing staff. An adjustable article of furniture is generally equipped with a motor drive in the form of electrically driven linear actuators. In order to activate these, a control 1 is constructed which is operated by a hand control. The control is further designed to receive signals from a variety of connected equipment, such as e.g., a sensor which detects whether the patient currently occupies the bed. It could also be sensors which detect whether the bed needs cleaning, either a routine cleaning or an extraordinary cleaning if a sensor registers that the bed is wet. In FIG. 1 the control 1 is connected to the gateway 2 by means of the OPENBUS™ system. The gateway thus both receives information in the form of the messages generated by the control and the messages generated by the patient by means of the operating panel. For explanation of how the messages from the patient are generated, the operation panel is equipped with the possibility for a call function, which the patient can use to call the nursing staff for help for various tasks, where the various tasks are described on the operation panel with text or icons. As it further appears from FIG. 1, the gateway 2 converts the signal from the control 1 into a format which is sent from a built-in GSM modem. The gateway is thus configured to send data strings to a receiver, which may be a mobile telephone 3 connected to the GSM network or a modem 4 connected to the GSM network. Where a receiver terminal in the form of a mobile telephone 3 is concerned, messages in the form of SMS, EMS or MMS are sent, which can be received directly by the terminal and shown on a display. When receiving a MMS it is further possible to play an audio file. This is particularly expedient since the nursing staff, when it receives a message, is often occupied by another nursing task, which cannot easily be interrupted, even briefly. The mobile telephone may thus be configured to automatically play an incoming message, so that the nursing staff receives the message immediately as speech, directly from the loudspeaker of the mobile telephone or a headset. The nursing staff can thus immediately determine how the incoming request for care should be prioritized. In case of acute need for care they can change the visiting route to prioritize the patient. When the nursing staff receives the request they have to acknowledge receipt within a certain period of time. The receipt is sent directly to the gateway 2 of the patient, which communicates the information to the control 1, so that this can indicate that the request is complied with and prevent that the patient feels ignored and thus induced to send the same request again and again until the nursing staff arrives.

Besides the mobile telephone 3 of the nursing staff, the system consists of a server 5, which receives a copy of all sent requests in the system. It is noted that the server as shown in the drawing receives data from the gateways 2 of several patients and also data from the mobile telephones of the nursing staff 3. In the drawing a number of ten gateways is outlined, but the system is not limited to that number. The server receives the requests via a SMS gateway 6, which is equipped with a modem 4. The SMS gateway can directly receive SMS messages and convert these into a file, but can also receive data packages via GPRS, which are processed and forwarded as files. The connection between the SMS gateway 6, the server 5 and other connected units, such as, e.g. a super user 7 for the system or service personnel 8 is conducted via LAN, which is extended to also cover wireless terminals. Further, it is possible for the SMS gateway to send SMS/MMS from the system. Units receiving such messages in the system are the gateway 2 of each patient but also mobile telephones 3,9 of the nursing staff and service personnel. Further, it is possible to send messages via the internet directly from the serves, typically in the form of e-mails, to outside service personnel 10. This could be personnel in charge of a specific service task in connection with the article of care furniture or similar tasks which may be contracted out.

The system is designed so that all transactions are logged in a data file on the server. The program, which is processed in the server, is a database program, which also continuously sorts the incoming messages and forwards them to the relevant party. In connection with the task specified in the message the system also keeps track of the status of the task and which attendant is responsible for carrying out the task. This is possible in that the system receives a copy of all the messages sent between the patient and nursing staff, including the receipts of the nursing staff of a received, commenced and completed task. It is thus possible constantly to keep track of which outstanding care and service tasks there are in the system. Further the system contains the duty rosters for the nursing staff and the telephone numbers for the mobile telephones of the nursing staff. When the patient is concerned there is a telephone number for the mobile telephone 3 of the nursing staff in the local gateway 2 and a telephone number for the modem 4 in the SMS gateway 6 for the monitoring system 12*a*. When receiving a message from the SMS gateway, these numbers can be changed so that messages from the patient are always sent to the mobile telephone which follows the nursing staff according to the duty roster.

Figure 2:
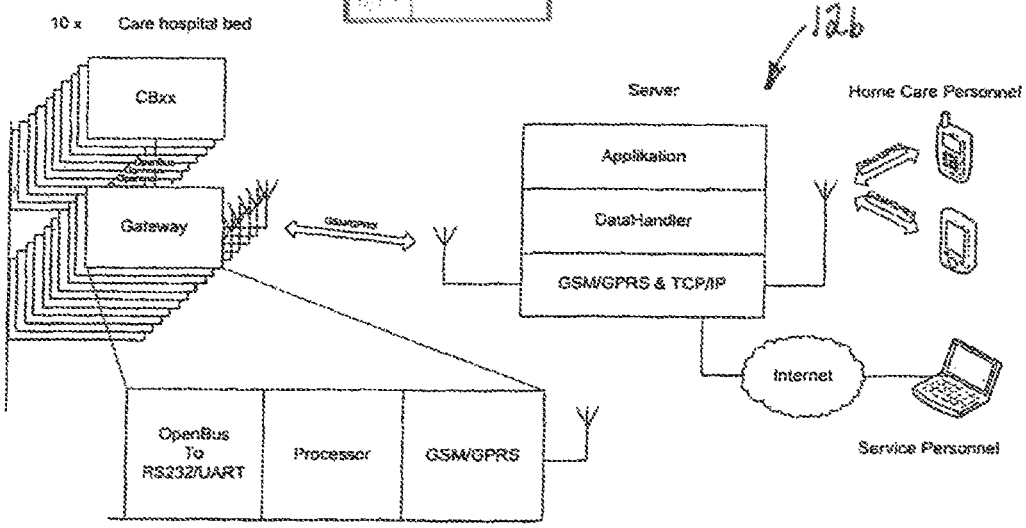
FIG. 2 shows an alternative structure of the communications system.

As shown in FIG. 2, the system may be designed in an alternative way, where all communication is conducted via the monitoring system 12*b*. The messages in the system 12*b* are the same except for the duty roster, which does not necessarily have to be distributed to the gateway of the patients when the duty roster is changed. For the gateway 2 of the patient it is advantageous that messages should not necessarily be sent as SMS via the GSM system, but also can be sent as packages via GPRS to the monitoring system 12*b*.

Figure 3:
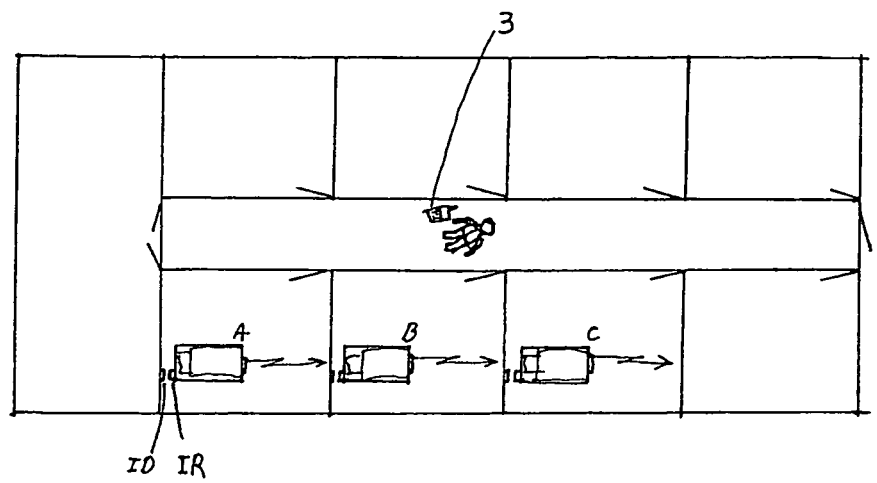
FIG. 3 shows a systems specification of a further embodiment of the communications system.

In FIG. 3 is schematically shown a further embodiment of the communications system with a dynamic addressing. In a wing or floor of a building there are a number of wards or apartments with a bed A, B, C . . . for the care-requiring residents. The beds are equipped with a short-range wireless data network (WPAN) such as Bluetooth. This can, e.g., be integrated in an ACP (Attendant Control Panel). When e.g., a random attendant such as a nurse, an assistant nurse, a cleaning worker or a service worker is within reach of the wireless data network, it would automatically detect the mobile telephone of that person, so that that person is moved to the top of the current list in the system of the personnel on duty. In case one of the patients or residents calls for help the person in question will then receive a message instead of the person dedicated to a certain area, who in reality may be far from the place. Hereby, the patient first and foremost receives quick assistance and the attendant can form an idea of the situation and maybe immediately solve the problem or call the dedicated person responsible for the area with a message of whether the situation is acute or may be incorporated into the usual routine. Thus, the commuting time of the nursing staff, which by definition is wasted time, may be minimized.

In multi-storey buildings a wireless data network such as Bluetooth can, e.g., detect the mobile telephone of an attendant on an upper or lower floor or a neighbouring building. This problem may be solved with an identification of the beds. A way to do this is by means of IRID, where the beds, e.g., at the head of the bed are equipped with an IR scanner, which detects a unique ID bar code located on the wall where the bed is positioned. Another possibility for identification is RFID, e.g., passive tags.

It should be understood that the communications system can be configured in various ways e.g. by means of a Piconet in different bed units, constituting a slave network, which may be connected to a superior Scatternet.

The invention claimed is:

1. A communications system for exchanging data between a patient in an article of care furniture and a nursing staff or service personnel which manages a nursing task for the patient or a service function of the article of care furniture, the communications system comprising:
   an operation panel,
   a control connected to the operation panel and configured to generate one or more signals indicative of at least one of the status of the patient, the status of the article of care furniture, and a patient request associated with the nursing task,
   a gateway, to which the control is connected, configured to receive the one or more signals from the control via an interface, said gateway configured to convert the one or more signals into information having a format wherein said gateway comprising a modem for sending the information in the converted format via a mobile telephone network to a receiver connected to the mobile telephone network, where the communication is carried out by exchanging data in the form of data strings, and wherein the receiver is configured to recover a received data string,
   a monitoring system in communication with the receiver including a computer which is equipped with a program code for processing a database program, and wherein said monitoring system is configured to forward the received data string to a specific recipient based on data in the received data string.

2. The communications system according to claim 1, wherein the receiver is a first receiver, further including a second receiver, and wherein the communication is conducted as a message.

3. The communications system according to claim 2, wherein a respective telephone number for the first and second receivers of data strings is stored in the control and is updated when a configuration message is received.

4. The communications system according to claim 2, wherein the second receiver is a mobile telephone, and a data string received by the second receiver is shown on a display of the mobile telephone.

5. The communications system according to claim 3, wherein the second receiver of a data string is configured to send an acknowledgement of receipt of the data string.

6. The communications system according to claim 2, wherein the first receiver includes a modem which transmits data strings for processing in the monitoring system.

7. The communications system according to claim 6, wherein the program code is configured for processing a database program with respect to at least one log file.

8. The communications system according to claim 2, wherein the monitoring system receives data strings with receipts from the second receiver which indicates that a request for execution of a task has been received, commenced and completed by a nursing staff associated with the second receiver.

9. The communications system according to claim 1, wherein the information concerning a geographical location of the gateway is sent to the monitoring system.

10. The communications system according to claim 4, wherein said second receiver comprising the mobile telephone is configured to convert the received text string into an audio signal corresponding to speech.

11. The communications system according to claim 10, wherein the modem is a global system for mobile communications modem equipped with an input with analog-digital converter and an output with digital-analog converter and a control which controls the routing of speech information.

* * * * *